United States Patent [19]

Shefer et al.

[11] Patent Number: 4,887,604
[45] Date of Patent: Dec. 19, 1989

[54] APPARATUS FOR PERFORMING DUAL ENERGY MEDICAL IMAGING

[75] Inventors: Ruth Shefer, Waban; Robert E. Klinkowstein, Winchester; Richard Petrasso, Cambridge, all of Mass.

[73] Assignee: Science Research Laboratory, Inc., Somerville, Mass.

[21] Appl. No.: 194,190

[22] Filed: May 16, 1988

[51] Int. Cl.$^4$ .............................................. A61B 6/00
[52] U.S. Cl. ..................... 128/654; 378/62; 378/144; 378/156; 128/659
[58] Field of Search ............ 378/51, 62, 99, 143, 378/144, 156; 128/653, 654, 659

[56] References Cited

U.S. PATENT DOCUMENTS

| | | | |
|---|---|---|---|
| 2,919,362 | 12/1959 | Atlee | 378/143 |
| 3,854,049 | 12/1974 | Mistretta et al. | 378/62 |
| 3,860,817 | 1/1975 | Carmean | 378/62 |
| 3,920,999 | 11/1975 | Drexler et al. | 378/143 |
| 3,974,386 | 8/1976 | Mistretta et al. | 378/99 |
| 4,158,770 | 6/1979 | Davis, Jr. et al. | 378/62 |

FOREIGN PATENT DOCUMENTS 8303674 10/1983 PCT Int'l Appl. ................ 378/143

*Primary Examiner*—Kyle L. Howell
*Assistant Examiner*—Krista M. Pfaffle
*Attorney, Agent, or Firm*—Wolf, Greenfield & Sacks

[57] ABSTRACT

An energy substraction medical imaging system which is used for imaging a body part impregnated with a radio-opaque dye such as iodine is provided. The system includes an electron beam target having a target surface which, when excited by a high-energy electron beam, generates radiation having strong $K_\alpha$ at energy levels slightly above and slightly below the K-edge energy level of the dye. The target surface is preferably formed of a compound containing lanthanum, such as lanthanum oxide. The target may also be formed of a compound containing a material having a $K_\alpha$ line at an energy level slightly above the dye K-edge and a material with $K_\alpha$ line slightly below the dye K-edge or with separate sections containing such materials which are alternately excited. The target is excited by a high-energy electron beam from a suitable source, the electron beam having sufficient energy to provide a high photon yield at the $K_\alpha$ line energy levels and sufficient power to produce the required photon fluences at such energy lines for the medical imaging application. One of the $K_\alpha$ lines in the radiation output from the excited target is selectively filtered and the output from the filter, both with the $K_\alpha$ line filter and with the line unfiltered, are passed through the body part being imaged to an x-ray detector. The output from the detector in response to the filtered and unfiltered outputs is processed to obtain an image of the body part. Continuum radiation from the target is reduced by filtering the continuum radiation at frequencies above the below the $K_\alpha$ line energy levels of the target compound, by viewing the radiation from the target in the backward direction to the beam, and by having the thickness of the target equal to a fraction of the electron range in the target compound material.

21 Claims, 3 Drawing Sheets

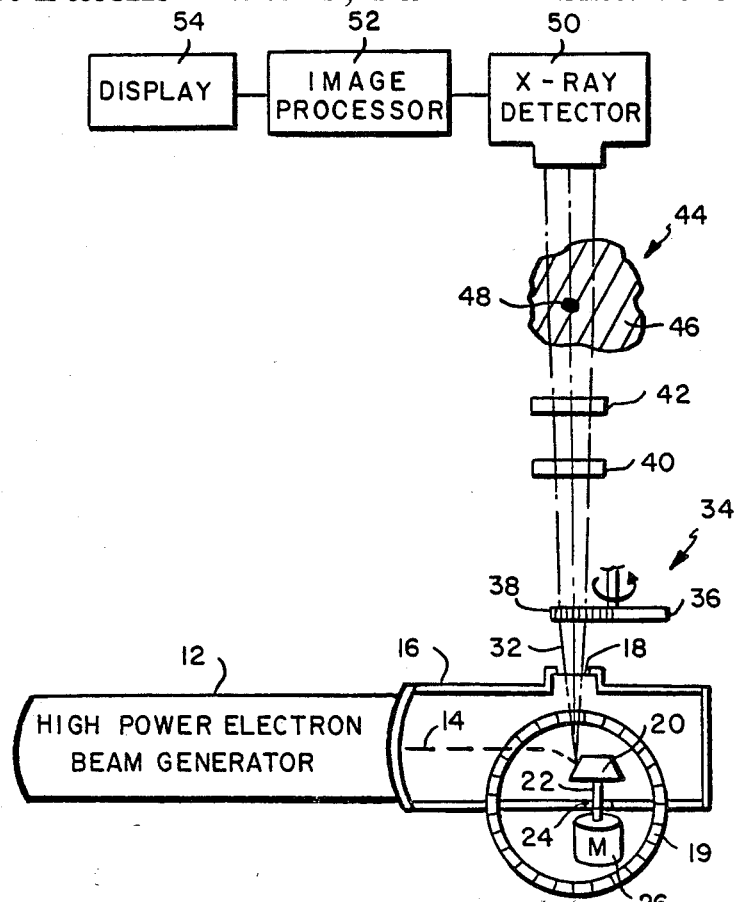
FIG. 1
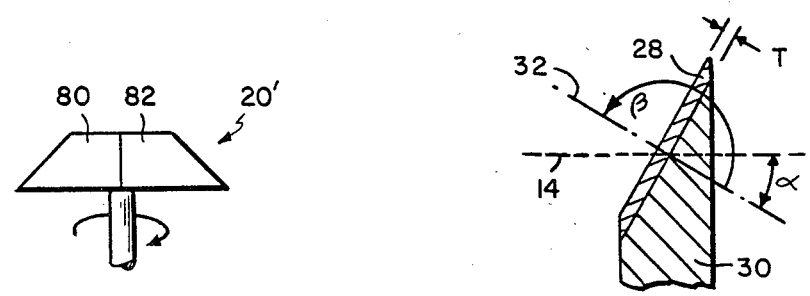
FIG. 6
FIG. 2

APPARATUS FOR PERFORMING DUAL ENERGY MEDICAL IMAGING

FIELD OF THE INVENTION

This invention relates to methods and apparatus for dual energy medical imaging and more particularly to a system for doing energy subtraction angiography using an iodine-based radio-opaque dye.

BACKGROUND OF THE INVENTION

Since many body structures are composed of substantially the same tissue substances, it is generally difficult to differentiate such parts in an x-ray image. To permit easier viewing of selected body structures, a radio-opaque dye or contrast agent is frequently applied to such structure before the x-ray is taken. For example, conventional coronary anteriograms are generally acquired by inserting a catheter into a patient's peripheral artery and feeding the catheter through the arterial system to the heart. The physician then positions the tip of the catheter, under the guidance of an x-ray fluoroscope image, in the artery of interest, and a bolus of undiluted iodine contrast agent is injected through the catheter into the artery. The resulting high-quality x-ray image of the artery reveals the geometry of the arterial wall and allows, among other things, the identification of regions where blood flow may be reduced because of a blockage.

The complicated coronary angiography procedure described above is necessary because of the low sensitivity of conventional x-ray imaging systems to iodine-based contrast agents. This procedure is, however, both costly and hazardous. The catheterization procedure may cause myocardial infarction or stroke and the high concentration of the iodine dye may cause kidney problems including renal failure. The catheterization requires that the procedure be performed in an operating room with the patient normally being in the hospital for two days. As a result, the cost of the procedure can be several thousand dollars.

Because of both the costs and risks indicated above, coronary angiograhy is not normally utilized as a diagnostic or screening tool, but is reserved only for symptomatic patients where coronary artery disease may already have reached an advanced stage. Since coronary artery disease and its complications are the most common cause of death and disability in the middle-aged and elderly American population, a need exists for an improved method and apparatus for performing this procedure so as to reduce both the costs and the risks involved, thus permitting the procedure to be more extensively used. In particular, the improved procedure should permit the costs and risks to be reduced to the point where coronary angiography could be utilized as a routine diagnostic and screening tool.

One technique which has been employed for reducing the amount of iodine required to do coronary angiography is energy-subtraction imaging which takes advantage of the abrupt K-edge discontinuity in the iodine x-ray absorption spectrum to increase the sensitivity of the imaging system to body structures which have been iodinated. The K-edge discontinuity results from the absorption of an x-ray photon by an electron in the $K_\alpha$ shell of the iodine atom resulting in ionization and permitting an electron from the L shell to fall into the $K_\alpha$ shell vacancy. Because of this discontinuity, if images are taken at energy levels slightly above and slightly below the K-edge within a short time period compared to a heart cycle, and these images are logarithmically subtracted, the contrast produced by noniodinated structures cancel, whereas the contrast due to the iodinated structures remains due to the difference in the iodine absorption coefficient of the two images. Since this technique permits the removal of shadow images caused by bone, tissue and the like, it theoretically permits high-quality arteriograms to be produced using low concentrations of iodine-contrast agent. Reductions in required concentration of the iodine-contrast agent by a factor of approximately 25 may be possible utilizing this technique, permitting the iodine-contrast agent to be injected into a vein and flow to the desired heart area. This high reduction in concentration factor is necessary in order to employ the contrast agent in this way, because of the substantial dilution of the contrast agent as it flows from the injection site to the site where the image is to be taken. It is also desirable to reduce the amount of iodine contrast agent initially required. This procedure thus has the potential for substantially reducing risk factors in the angiograhy procedure by eliminating the need for a catheter and by reducing the iodine concentration level required. It would also reduce the cost of the procedure by making it possible for the procedure to be performed on an outpatient basis. The combination of improved safety and reduced cost might make the procedure available for screening use in nonsymptomatic cases, and to monitor progress after various coronary treatment procedures.

However, conventional broad-band x-ray sources with energy filtering or dual electron beam energies have been unable to provide the required photon fluences for energy subtraction imaging of the human coronary arteries. Narrow band x-ray beams from synchrotron sources with monochromators have produced high quality images. However, the costs associated with even a small synchrotron facility are currently about $30,000,000, a cost which is prohibitively high for most clinical applications. A need therefore exists for an improved apparatus and procedure for performing dual energy or energy-substraction medical imaging, and in particular energy subtraction coronary angiography, which permits this procedure to be performed at a cost which is consistent with that of comparable medical equipment.

SUMMARY OF THE INVENTION

In accordance with the above, this invention provides an energy subtraction or dual energy medical imaging system which may be used for imaging a body part impregnated with a radio-opaque dye. The system includes an electron beam target having a target surface which, when excited by a high-energy electron beam, generates radiation having strong $K_\alpha$ lines at energy levels slightly above and slightly below the K-edge energy level of the dye. A high energy electron beam is provided to excite the target. The electron beam should have sufficient energy to provide a high photon yield at the $K_\alpha$ line energy levels and sufficient power to produce the required photon fluences at such energy lines for the medical imaging application. At least one of the $K_\alpha$ lines in the radiation output from the excited target is selectively filtered. The output of the filter with both the $K_\alpha$ line filtered and without the $K_\alpha$ line filtered, are passed through the body part being imaged to an x-ray detector. The output from the detector in response to the filtered and unfiltered outputs are processed to obtain an image of the body part. The radio-opaque dye preferably contains iodine and the target is preferably a compound containing lanthanum. The preferred target compound is a thin layer of lanthanum oxide. Continuum radiation from the target is reduced by filtering the continuum radiation at frequencies above and below the $K_\alpha$ line energy levels of the target compound, by viewing the radiation from the target in the backward direction to the beam and by having the thickness of the target equal to a fraction of the electron range (R) in the target compound material. The invention also includes means for protecting the target from overheating, including rotating the target and keeping the thickness of the target compound thin enough so that most of the energy loss from the electron beam occurs after the electron beam passes through the compound.

The foregoing and other objects, features and advantages of the invention will be apparent from the following more particular description of the invention as illustrated in the accompanying drawings.

IN THE DRAWINGS

FIG. 1 is a diagram, partially in block form, of a dual energy imaging system employing the teachings of this invention.

FIG. 2 is an enlarged sectional view of a portion of a target suitable for use in the embodiment of FIG. 1.

FIG. 6 is an enlarged side view of an alternative target for use in the system of FIG. 1.

DETAILED DESCRIPTION

Figure 3:
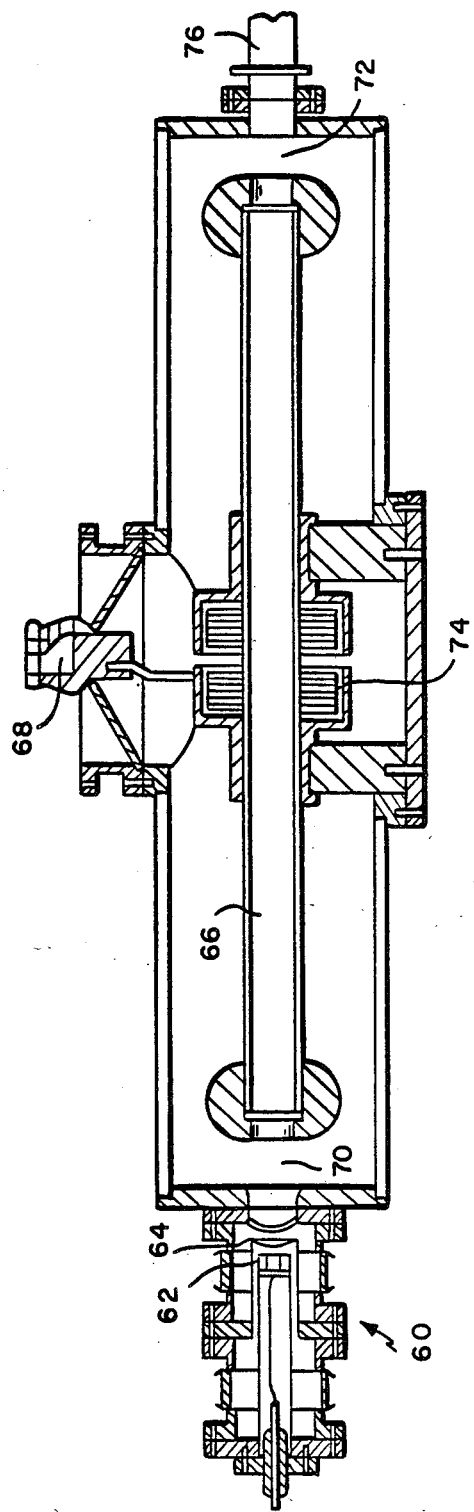
FIG. 3 is a diagram of an RF electron linear accelerator suitable for use as the high-power electron beam generator which is the embodiment of the invention shown in FIG. 1.

Referring to FIG. 1, a medical imaging system suitable for practicing the teachings of this invention is shown. The system includes a high-power electron beam generator 12, the electron beam output 14 from which is applied to an evacuated x-ray tube 16. The exact nature of generator 12 does not form part of the present invention. However, the generator should be capable of generating an electron beam having an electron energy sufficient to provide a high photon yield (preferably a yield near peak value) at the desired $K_\alpha$ line energy levels and sufficient power to produce the required photon fluences at such energy lines for the medical imaging application. An electron energy of approximately one MeV with an average current of 0.5 to 1.0 amperes in a 5 ms time period is an example of suitable parameters for the generator where the target compound is lanthanum or lanthanum oxide. While photon yields might be adequate at energies as low as 80 KeV, power requirements at such energies in order to achieve the required photon fluence would be high and could cause target damage. For this reason 500 KeV may be a practical lower limit for the electron beam. For a lanthanum target near maximum photon yields are obtained at energy levels of 1 to 4 MeV; however, radiation shielding considerations and available generators suggest using energies at the lower end of this range. For other target compounds, slightly different energies and power may be required. The electron beam 14 could be continuous, but is preferably pulsed at a rate of, for example, 30 hz or 60 hz. An example of an electron beam generator suitable for use as generator 12 is a compact, single resonator radio frequency (RF) accelerator of the type described in greater detail hereinafter.

Tube 16 attaches to generator 12 in a manner such that a vacuum may be maintained in both components. The shell of tube 16 is formed of stainless steel or other suitable material and is preferably opaque except at a rearward-facing window 18. The electron beam entering tube 16 is bent at a 90° angle by bending magnets 19 before impinging on target 20. Target 20 is in the shape of a frustum and is mounted for rotation on a shaft 22. Shaft 22 projects through a seal 24 in tube 16 and is rotated by a suitable means such as motor 26. For reasons which will be discussed in greater detail hereinafter, target 20 may be rotated at a rate of, for example, 100 cycles per second.

Referring also to FIG. 2, it is seen that target 20 has a thin layer 28 of a compound generating the desired $K_\alpha$ lines in response to the applied electron beam plated, glued or otherwise secured around the full 360° of its angled side. The layer 28 is backed by a low Z refractory material 30 (i.e. a material having good thermal properties) such as graphite. The thickness of the layer 28 should be a small fraction of the electron range (R) for the material 28. The electron range for a material is the approximate distance in the material at which an electron will come to rest, and is a standard number for each material. The thickness T of the layer 28 is preferably in the range of 0.1R to 0.3R. For the preferred embodiment, the layer 28 is formed of a lanthanum compound, such as lanthanum oxide. As will be discussed in greater detail later, lanthanum has $K_\alpha$ lines at values just above and just below the K-edge energy level for iodine.

Referring still to FIG. 2, the angle $\alpha$ between the perpendicular to the surface of target layer 28 and the direction of the output radiation 32 should preferably be as small as possible. Conversely, the angle $\beta$ between the direction of the electron beam 14 and the direction of the beam of output radiation 32 from the target should be as large as possible. More particularly, the angle $\beta$ should be in the range of 120° to 180°. For the preferred embodiment, $\alpha$ equals 15° and $\beta$ equals 180°.

The output radiation 32 from the target compound layer 28 contains both $K_\alpha$ lines of interest. While for reasons which will be discussed in greater detail hereinafter, continuum radiation at energy levels other than the desired $K_\alpha$ levels is minimized in the beam 32, the beam still contains some continuum radiation. The radiation 32 passes in the backward direction through window 18 of tube 16 to iodine filter 34. Iodine filter 34 is rotatable so as to present either a region 36 or an iodine filter region 38 to beam 32. When the region 36 of filter 34 is presented to the beam 32, both the high energy and low energy $K_\alpha$ lines pass through the filter, while when the filter is rotated to cause the beam 32 to pass through the iodine side 38 of the filter, only the low energy $K_\alpha$ line passes through the filter. The iodine filter region 38 may for example consist of iodine in a concentration of 100 mg/cm². It is noted that the iodine filter will also result in some reduction in the intensity of the low-energy $K_\alpha$ line output which can be compensated for.

The radiation passing through filter 34 may then be passed through two additional filters 40 and 42, one of which is formed of a low Z material such as aluminum for attenuation of any continuum radiation in the beam which is below the energy level of the desired low energy $K_\alpha$ line, and the other of which is formed of a high-energy x-ray absorbing material such as cerium with an absorption edge above the $K_\alpha$ lines of the target compound 28. The filters 40 and 42 are thus effective to substantially attenuate any continuum radiation remaining in the beam. This has the desirable effects of improving the signal to noise ratio in the resulting output, and of reducing the radiation received by the patient.

It is noted that while, for purposes of illustration, a separate high-energy filter, for example the filter 42, has been shown in FIG. 1, this filter is not necessarily required when the beam is passing through iodine filter 38, since this filter is operative to remove a substantial portion of the radiation above the K-edge level of the iodine. Thus, while region 36 of filter 34 may be clear, this region is preferably formed of a cerium filter so that with filter 34 in its iodine position, high-energy continuum radiation is attenuated by region 38 of the filter, while when the filter is in its other position, high-energy continuum radiation is attenuated by the cerium in region 36 of the filter. With this configuration, a separate cerium filter 42 is not required. A cerium filter suitable for use either in the region 36 of filter 34 or as a separate filter 42 would be one having a cerium concentration of 50 mg/cm².

The filtered radiation which is substantially restricted to radiation at the desired $K_\alpha$ energy levels is applied to the region of the body 44 being examined, such region containing tissue and bone 46 which is not of interest, and the iodinated artery or other body structure 48. Filter 34 is operated quickly enough so that both iodine filtered radiation and radiation which is not iodine filtered, and thus contains both $K_\alpha$ lines, are applied to body area 44 within a ten millisecond interval, an interval short enough so that heart, blood or other movement occuring within the body area would not be a factor in the image processing.

The radiation passing through body 44 is detected by a standard x-ray detector 50 which digitizes the received analog signals for application to image processor 52. Image processor 52 could be a specialized piece of hardware adapted to perform the energy subtraction imaging function. However, for most applications, processor 52 would be a general purpose processor, for example a micro- or mini-processor, programmed to perform this function. The processor may either be dedicated to performing the energy subtraction function, or this may be one of many functions performed by the processor. The image processor is adapted to scan and store both a filtered and an unfiltered frame, and to then determine the intensity at each pixel location of the frame by determining a difference value D at such location according to the formula:

$$D = w \ln(I_L/I_{LO}) - \ln(I_H/I_{HO}) \qquad \text{(Eg. 1)}$$

where
- $I_L$ = the energy received from the low $K_\alpha$ line radiation
- $I_{LO}$ = the energy incident in the low $K_\alpha$ radiation spectrum
- $I_H$ = the energy received from the high $K_\alpha$ line radiation
- $I_{HO}$ = the energy incident in the high $K_\alpha$ radiation spectrum and the measured signals are $I_1 = I_L + I_H$ (i.e. the unfiltered signal)

$I_2 = I_L$ (i.e. the intensity of the filtered signal)

and W is the ratio of the high energy to low energy tissue attenuation coefficient. The output from image processor 52 is applied in a standard manner to control the display on a display device 54 such as a cathode ray tube monitor. The output from image processor 52 may also be utilized to expose film or to cause some other form of hard copy of the image to be produced.

FIG. 3 shows a fixed-frequency RF accelerating resonator which is suitable for use as the high-power electron beam generator 12. A resonator of this type is for example described in a paper entitled "Energy Saver Prototype Accelerating Resonator" by G. Kerns et al, which was published in the *IEEE Transactions on Nuclear Science*, Vol. NS-28, No. 3, June 1981. As previously indicated, the accelerator should, for the preferred embodiment using a lanthanum target, be capable of supplying a macropulse of electron current which is 5 to 10 ms in duration with a peak energy of 1 MeV and an average current of 0.5 amperes. The accelerator should preferably be capable of delivering the macropulses at a rate of at least 30 Hz.

Referring to FIG. 3, the accelerator has a 3 ampere, 13.5 kV electron gun injector 60 having a dispenser cathode 62 which is modulated at a desired frequency, for example 70 MHz, by a control grid 64. The input power is coupled to an RF transmission line resonator 66 by a tap which is positioned to provide the proper impedance match to an RF power source 68. The RF power source produces a 70 MHz standing wave which causes one-half of the total accelerating energy to be produced at each of accelerating gaps 70 and 72 spaced $\pi$ radians apart. Each half of the accelerator comprises a one-quarter wavelength transmission line resonator which is excited by the centrally fed coaxial line. A resistive mode suppressor 74 is located at the center of resonator 66 and functions to damp out unwanted out-of-phase cavity modes. These unwanted modes result in deceleration in the second gap 72 and are characterized by a current maximum at the center of the drift tube. The output micropulse from the system is applied through tube 76 to x-ray tube 16. This pulse will have an energy in the 1.0 MeV range with a pulse duration of 8.2 nanoseconds.

Figure 4:
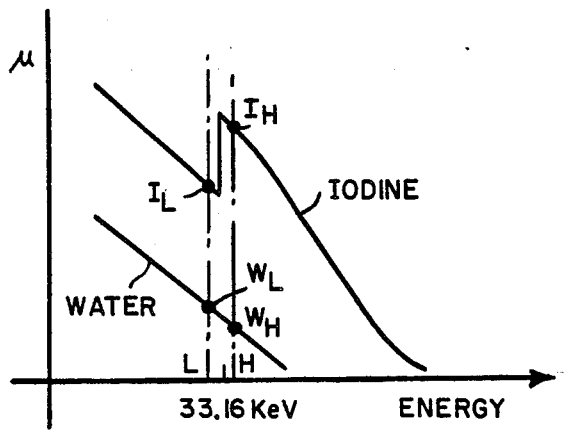
FIG. 4 is a chart illustrating the absorption spectrum for iodine and water in the electron energy range of interest.

Referring to FIG. 4, a chart is shown illustrating the absorption characteristics of iodine and water at the energy levels of interest. From FIG. 4 it is seen that, while the absorption characteristic for water is linear in this region, the absorption characteristic for iodine has a sharp K-edge at 33.16 KeV. Thus, if an image were taken at an energy level L slightly below the iodine K-edge value and at substantially the same instant an image was taken at energy level H slightly above the K-edge value, from FIG. 4 it is seen that the two readings, WL and WH for water, the primary substance making up body tissue, would cancel each other when one is subtracted from the other. However, the sharp K-edge at 33.16 KeV results in there being a substantial difference in the absorption values for IL and IH, such that when one of these values is subtracted from the other, a substantial difference value exists. It should be understood that in FIG. 4 the spread between the L and H energy levels has been exaggerated fo easier viewing, and that in practice there would be substantially no difference between WL and WH, resulting in the total cancelation of these values, permitting iodinated body structures to be easily differentiated, even with relatively low iodine contrast agent concentrations.

Figure 5:
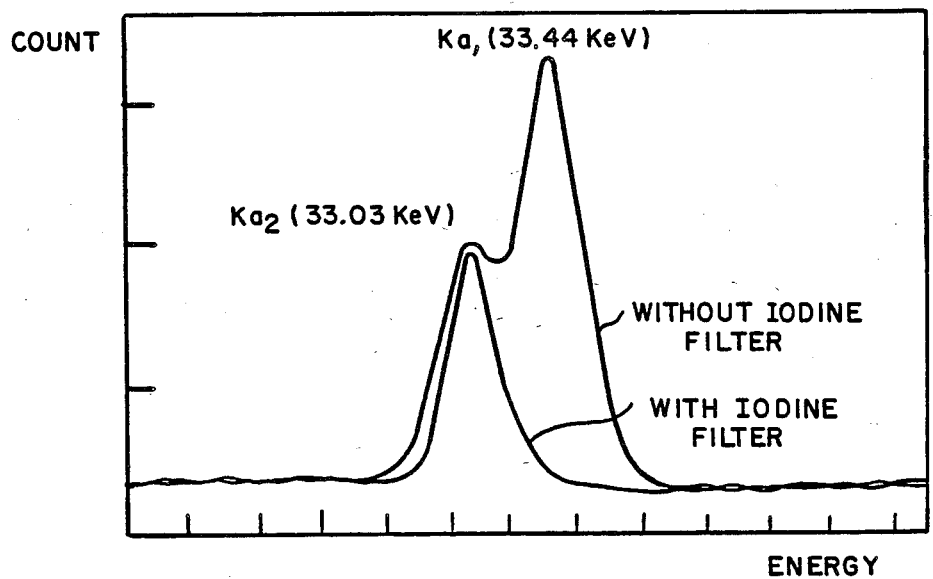
FIG. 5 is a chart illustrating the $K_\alpha$ output lines for lanthanum with and without filtering.

FIG. 5 illustrates the emission radiation from the lanthanum target layer 28 which is applied to body 44 without iodine filter region 38 in place, and with this filter region in place. The emission radiation shown in FIG. 5 has had the continuum radiation at energy levels above and below the desired $K_\alpha$ energy levels substantially suppressed. From FIG. 5, it is seen that lanthanum has a $K_\alpha$ line at a value of 33.44 KeV which is slightly above the 33.16 KeV K-edge energy value for iodine, and a $K_\alpha$ output at an intensity which is roughly half that of the $K_\alpha$ output at an energy level of 33.03 KeV, a value slightly below the K-edge energy level of iodine. The energy bandwidth of these two lines is approximtely 15 eV, and their energy separation is approximately 410 eV. With iodine filter region 38 in place, the $K_\alpha$ line is substantially absorbed. However, the $K_\alpha$ line passes through the iodine filter with a degree of attenuation which depends on the characteristics of the filter. For the iodine filter previously described, roughly half of the energy of the $K_{\alpha 2}$ line would remain after passing through filter region 38.

The quality of the results obtained using the procedures of this invention will depend on the ability to obtain high contrast between iodinated structures and background bone and tissue, and on low signal-to-noise ratio. High contrast is achieved by having the $K_\alpha$ lines which are utilized to do the imaging be as close in energy as possible to the K-edge energy level of the contrast agent in the dye, in this case iodine. The $K_\alpha$ lines of lanthanum are, as previously indicated, spaced by only 410 eV from each other. The low energy $K_\alpha$ line for lanthanum is only 130 eV below the K-edge energy level of iodine while the higher energy $K_\alpha$ line is only 280 eV above the K-edge level. These values are sufficiently close to assure that substantially all non-iodinated structures cancel in the subtraction process of equation (1) while the iodinated structures will have sufficient contrast to be visible.

Reducing the continuum radiation in the image serves to both improve the signal-to-noise ratio and to also improve contrast by eliminating undesired images which may be caused by continuum radiation. In the invention, continuum radiation is reduced in a number of different ways. First, continuum radiation is strongest in the direction the electron beam is traveling, and is weakest in the backward direction. By viewing the radiation from the lanthanum target in a direction 180° from the electron beam direction, minimum continuum radiation appears in the beam 32 outputted from tube 16. Filters 34 and 40 are then utilized to reduce both continuum radiation above the high $K_\alpha$ line level and continuum radiation at energies below the low $K_\alpha$ line level. A filter 42 may be provided to filter high energy radiation if region 36 of filter 34 is not adapted to perform this function. Thus, to the extent any continuum radiation remains in the radiation applied to body 44 and detector 50, it is primarily in the energy region between the two $K_\alpha$ lines of lanthanum or closely adjacent thereto. The system is thus adapted to provide high-contrast images having a low signal-to-noise ratio.

Equation (1) is a simplified equation for the calculations which must be performed by image processor 52 in order to perform energy subtraction angiography. Factors must be added to this equation to take into account the roughly 2-to-1 difference in intensity level output between the high energy $K_\alpha$ line and the low energy $K_\alpha$ line of lanthanum. The processor must also take into account the reduction in energy level of the low energy $K_\alpha$ line caused by the filtering of this line by iodine filter region 38 which may cause the energy level of this line to be half that of the corresponding line unfiltered. However, these values are all constants which can be determined for a given system. Other factors which will need to be determined for each individual system include the actual energy levels, duration and repetition rate of the electron beam output 14 from generator 12, the optimum angle and thickness for target layer 28, and the rate and energy levels at which the system may be operated without causing damage to the lanthanum target layer 28. The latter point is particularly critical since lanthanum does not have good thermal properties. While certain lanthanum compounds such as lanthanum oxide have better thermal properties than pure lanthanum, the target can still be destroyed if the same point is repeatedly excited before it has had sufficient time to cool. Factors which must be taken into account in protecting the target layer against overheating include the energy and power of the electron beam 14 utilized, the rate at which target 20 is rotated, the diameter of the target, the thermal properties of the compound utilized for the layer 28, and the duration of operation of the system before the target is given an opportunity to cool. Once certain of these factors have been determined for a given system, such as the compound to be utilized as the target layer, and the diameter of the target, the remaining factors can be determined in order to avoid thermal damage of the target.

While for the preferred embodiment, the two $K_\alpha$ lines utilized are from a single compound such as lanthanum, it may also be possible to practice the invention using a target which is a compound of two elements, each of which produces one of the two required lines on either side of the iodine K-edge. For example, the target might be formed of a compound containing barium and cerium where the cerium generates the high-energy $K_\alpha$ lines at an energy level of approximately 34.5 KeV while the barium generates the low-energy $K_\alpha$ lines at an energy level of approximately 32 KeV. Other compounds might also be possible. FIG. 6 illustrates another alternative wherein the target 20' has a half 80 of the target surface formed of a first compound, for example a compound containing cerium, which generates the high-energy $K_\alpha$ line and a half 82 of a second compound, for example a compound containing barium, which generates the low energy $K_\alpha$ line. The target is rotated at a high enough speed so that both $K_\alpha$ lines are generated within the required time interval.

Thus, while the invention has been shown and described above with respect to a preferred embodiment, the foregoing and other changes in form and detail may be made therein without departing from the spirit and scope of the invention.

What is claimed is:

1. A dual energy medical imaging system for imaging a body part through which a radio-opaque dye is flowing, said dye having a predetermined K-edge energy level, comprising:

an electron beam target having a target surface which, when excited by a high-energy electron beam, generates a radiation output having strong $K_\alpha$ lines at energy levels slightly above and slightly below the K-edge energy level of the dye;

means for appling an electron beam to excite said target, said beam having sufficient energy to provide a high photon yield at the $K_\alpha$ line energy levels and sufficient power to obtain the photon fluence required for a medical imaging application;

filter means for selectively either filtering or passing unfiltered at least one of the $K_\alpha$ lines in the radiation output from the excited target surface;

an x-ray detector;

means for passing the output of said filter means with both said at least one $K_\alpha$ line filtered and said at least one $K_\alpha$ line unfiltered through the body part being imaged to said x-ray detector; and means for processing the energy received at the detector in response to the filtered and unfiltered outputs from the filtering means to obtain an image of the body part.

2. A system as claimed in claim 1 wherein said radioopaque dye contains iodine having a K-edge at 33.16 KeV; and wherein said target surface is formed of a compound containing lanthanum.

3. A system as claimed in claim 2 wherein said compound is lanthanum oxide.

4. A system as claimed in claim 1 wherein said radioopaque dye contains iodine having a K-edge at 33.16 KeV; and wherein said target surface is formed of a compound containing barium and cerium.

5. A system as claimed in claim 1 wherein a selected part of said target surface is covered with a first compound generating a strong $K_\alpha$ line at an energy level slightly above the K-edge energy level of the dye and another selected part of the target surface is covered with a second compound generating a strong $K_\alpha$ line at an energy level slightly below said K-edge energy level; and further comprising means for rotating the target surface to alternatively apply the electron beam to said first and second compounds.

6. A system as claimed in claim 5 wherein said first compound contains cerium and wherein said second compound contains barium.

7. A system as claimed in claim 1 wherein the energy of said electron beam is greater than 80 KeV.

8. A system as claimed in claim 1 wherein the energy of said electron beam is greater than 500 KeV.

9. A system as claimed in claim 8 wherein said electron beam has an energy of approximately 1 MeV.

10. A system as claimed in claim 9 wherein said electron beam has an average current over a 5 mS period of 0.5 to 1 amp.

11. A system as claimed in claim 1 wherein said electron beam applying means includes a radio frequency accelerating resonator.

12. A system as claimed in claim 2 further including means for reducing continuum radiation from the target.

13. A system as claimed in claim 12 wherein said means for reducing includes means for filtering continuum radiation from the target at frequencies above and below the $K_\alpha$ line energy levels.

14. A system as claimed in claim 12 wherein said means for reducing includes means for viewing the radiation from the target in the backward direction.

15. A system as claimed in claim 12 wherein said means for reducing includes the thickness of the compound used for said target being thinner than R, where R equals one electron range in the compound material.

16. A system as claimed in claim 15 wherein the target thickness is 0.1 to 0.3R.

17. A system as claimed in claim 1 including means for protecting the target from overheating.

18. A system as claimed in claim 17 wherein said means for protecting includes means for rotating the target.

19. A system as claimed in claim 17 wherein said means for protecting includes forming said target surface thin enough so that electrons of the electron beam pass through the surface before they sustain large energy loss, and a backing means for said target surface, said backing means having good thermal properties.

20. A system as claimed in claim 1 wherein said means for filtering filters the higher energy $K_\alpha$ line, resulting in an unfiltered image having energy $I_1 = I_L + I_H$; and a filtered image having an energy $I_2 = I_L$;

where $I_L$ and $I_H$ are the energy received at the lower energy $K_\alpha$ line and the energy received at the higher energy $K_\alpha$ line respectively; and wherein said means for processing determines the difference image by use of the equation $D = w \ln (I_L/I_{LO}) - \ln (I_H/I_{HO})$ where: $I_{LO}$ and $I_{HO}$ are energy incident at the low energy $K_\alpha$ line and the high energy $K_\alpha$ line respectively;

w is the ratio of the high energy to the low energy tissue attenuation coefficient.

21. A method for performing coronary angiography on a subject comprising the steps of:

placing an iodine dye at an appropriate point in the bloodstream of the subject, the iodine having a predetermined K-edge energy level;

exciting a target formed of a compound containing lanthanum with a high energy electron beam, the lanthanum generating strong $K_\alpha$ lines in response to the exciting electron beam at an energy level slightly above the iodine K-edge level and a level slightly below the iodine K-edge level; viewing radiation from said excited target in the backward direction;

selectively filtering the emitted radiation to remove energy emitted at a high $K_\alpha$ line of the lanthanum target radiation;

successively passing the filtered and unfiltered radiation from the target through a part of the subject's body to be imaged to a detector; and processing the detected radiation to determine the intensity in a difference image which represents the iodinated portion of the imaged body part;

whereby an image of the part of the subject s body containing the iodine dye may be obtained.

* * * * *